US008716526B2

(12) United States Patent
Okamoto et al.

(10) Patent No.: US 8,716,526 B2
(45) Date of Patent: May 6, 2014

(54) METHOD FOR PRODUCING DIFLUOROACETYL CHLORIDE

(75) Inventors: Masamune Okamoto, Fujimino (JP); Hideaki Imura, Iruma-gun (JP); Naoto Takada, Iruma-gun (JP)

(73) Assignee: Central Glass Company, Limited, Ube-shi (JP)

( * ) Notice: Subject to any disclaimer, the term of this patent is extended or adjusted under 35 U.S.C. 154(b) by 37 days.

(21) Appl. No.: 13/635,577

(22) PCT Filed: Mar. 16, 2011

(86) PCT No.: PCT/JP2011/056186
§ 371 (c)(1),
(2), (4) Date: Sep. 17, 2012

(87) PCT Pub. No.: WO2011/122341
PCT Pub. Date: Oct. 6, 2011

(65) Prior Publication Data
US 2013/0012740 A1    Jan. 10, 2013

(30) Foreign Application Priority Data

| Mar. 29, 2010 | (JP) | 2010-074639 |
| Apr. 8, 2010 | (JP) | 2010-089154 |
| Jun. 24, 2010 | (JP) | 2010-143716 |
| Feb. 1, 2011 | (JP) | 2011-019648 |

(51) Int. Cl.
C07C 53/40       (2006.01)
C07C 51/60       (2006.01)

(52) U.S. Cl.
USPC ............................ 562/840; 562/849; 568/407

(58) Field of Classification Search
USPC ................... 562/840, 849; 568/407
See application file for complete search history.

(56) References Cited

U.S. PATENT DOCUMENTS

| 4,357,282 A | 11/1982 | Anderson et al. |
| 5,710,317 A | 1/1998 | Oharu et al. |
| 2011/0065955 A1 | 3/2011 | Metz et al. |

FOREIGN PATENT DOCUMENTS

| EP | 0 293 747 A2 | 12/1988 |
| JP | 59-48435 A | 3/1984 |
| JP | 2-262530 A | 10/1990 |
| JP | 5-320091 A | 12/1993 |
| JP | 6-277510 A | 10/1994 |
| JP | 8-53388 A | 2/1996 |
| JP | 8-92162 A | 4/1996 |
| JP | 2010-64999 A | 3/2010 |
| WO | WO 96/29298 A1 | 9/1996 |
| WO | WO 2009/115426 A1 | 9/2009 |

OTHER PUBLICATIONS

Fukaya et al, J. Chem. Soc., Perkin Transl. 1, 1996, pp. 915-920.*

(Continued)

Primary Examiner — Kamal Saeed
Assistant Examiner — Janet L Coppins
(74) Attorney, Agent, or Firm — Crowell & Moring LLP

(57) ABSTRACT

A production method of difluoroacetyl chloride according to the present invention includes a chlorination step of bringing a raw material containing at least either a 1-alkoxy-1,1,2,2-tetrafluoroethane or difluoroacetyl chloride into contact with calcium chloride at a reaction enabling temperature. A production method of 2,2-difluoroethyl alcohol according to the present invention includes a catalytic reduction step of causing catalytic reduction of the difluoroacetyl chloride obtained by the above production method. By these methods, the difluoroacetyl fluoride can be efficiently converted to the difluoroacetyl chloride and to the 2,2-difluoroethyl alcohol.

10 Claims, 2 Drawing Sheets

(56) References Cited

OTHER PUBLICATIONS

Extended European Search Report dated Oct. 10, 2013 (five (5) pages).
Fukaya, H. et al., "Facile conversion of perfluoroacyl fluorides into other acyl halides", J. Chem. Soc., Perkin Trans. 1, 1996 pp. 915-920.
Parks, J. et al., "The Action of Alkanols on Tetrafluoroethylene" J. Am. Chem. Soc., 73, Mar. 1951 pp. 1329-1330.
PCT/ISA/237 (Jul. 2009).
International Search Report dated Jun. 21, 2011 with English translation (five (5) pages).

* cited by examiner

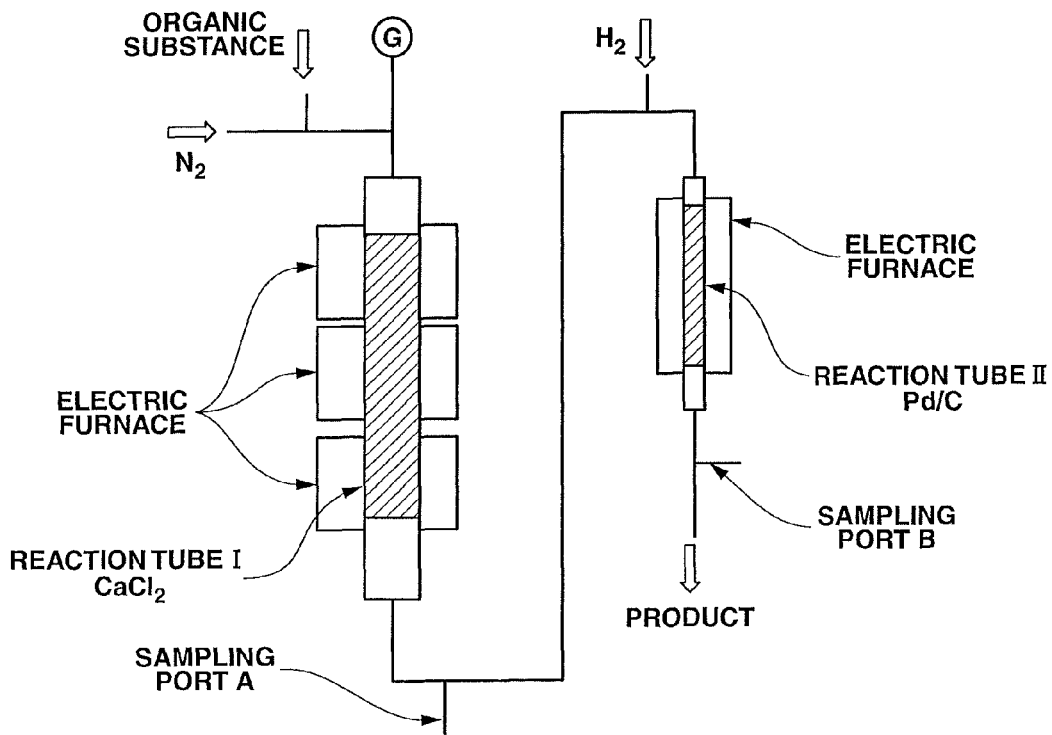
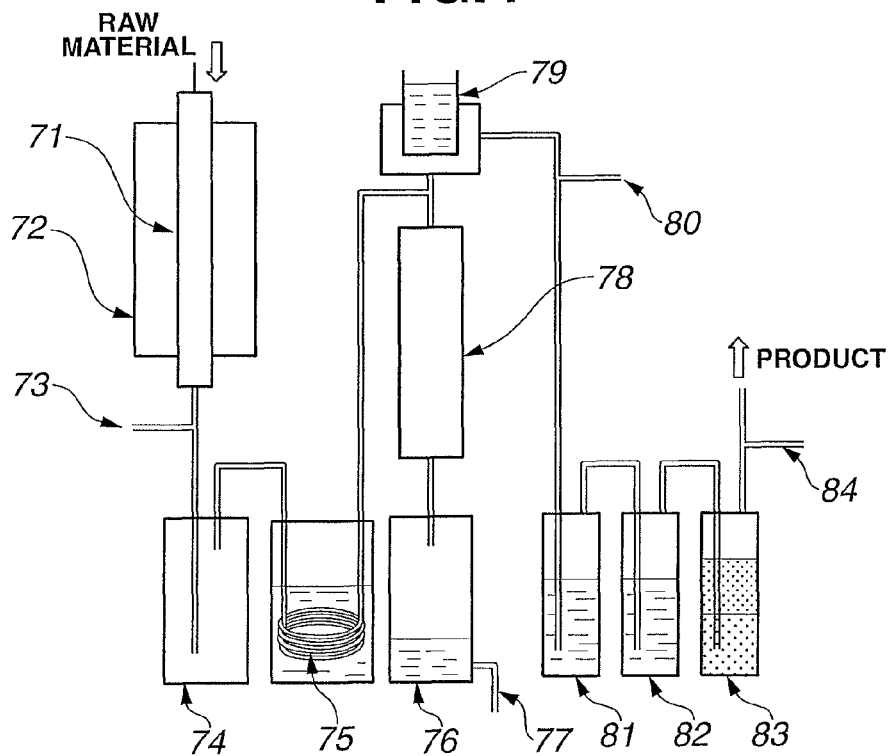

METHOD FOR PRODUCING DIFLUOROACETYL CHLORIDE

TECHNICAL FIELD

The present invention relates to a method for producing difluoroacetyl chloride (hereinafter sometimes abbreviated as "DFAC") and, more particularly, to a method for producing difluoroacetyl chloride by contact of a 1-alkoxy-1,1,2,2-tetrafluoroethane (hereinafter sometimes abbreviated as "ATFE") or a derivative thereof with calcium chloride.

BACKGROUND ART

It has been reported that difluoroacetyl chloride is useful as an intermediate for pharmaceutical and agrichemical products and as a reaction reagent, particularly a reagent for the introduction of a difluoromethyl group or difluoroacetyl group into an organic compound, and can be produced by various processes.

As a production method of a carboxylic acid chloride, there is generally known a process of reacting a carboxylic acid or a salt, ester or anhydride thereof with a chlorination agent such as chlorine, phosphorous pentachloride, phosphorous trichloride, phosphoryl chloride or thionyl chloride. It has been reported that difluoroacetyl chloride can be obtained by such a similar process. In this process, however, the raw material such as difluoroacetic acid or derivative thereof is not readily available.

By contrast, there is known a process of irradiating HCFC-132a (1,1-difluoro-3,3,3-trichloroethane), together with oxygen and chlorine, by a high-pressure mercury-vapor lamp under high-temperature conditions (Patent Document 1) as a method for producing a carboxylic acid chloride without going through difluoroacetic acid as an intermediate. In this process, the raw material is a substance that may cause ozone destruction. Further, this process is performed in a photoreaction system and thus is not so suitable for long-term production.

On the other hand, a process of thermally decomposing a 1-alkoxy-1,1,2,2-tetrafluoroethane (ATFE) in the presence of a metal oxide catalyst (Patent Document 2) and a process of decomposing a 1-alkoxy-1,1,2,2-tetrafluoroethane (ATFE) in the presence of an antimony pentafluoride catalyst under low-temperature conditions (Patent Document 3) are known as production methods of difluoroacetyl fluoride (hereinafter sometimes abbreviated as "DFAC"). A process of converting a perfluorocarboxylic acid fluoride to a corresponding acid chloride by halogen exchange reaction with lithium chloride (Non-Patent Document 1) and a process of forming benzoyl chloride by reaction of benzoyl fluoride with calcium chloride (Patent Document 4) have been reported as methods for direct conversion from carboxylic acid fluorides to carboxylic acid chlorides.

PRIOR ART DOCUMENTS

Patent Documents

Patent Document 1: Japanese Laid-Open Patent Publication No. H8-53388
Patent Document 2: Japanese Laid-Open Patent Publication No. H8-92162
Patent Document 3: U.S. Pat. No. 4,357,281
Patent Document 4: European Patent No. 293747
Patent Document 5: Japanese Laid-Open Patent Publication No. H6-277510

Non-Patent Documents

Non-Patent Document 1: J. Chem. Soc., Perkin Trans. 1, 1996, 915-920

SUMMARY OF THE INVENTION

Problems to be Solved by the Invention

It is an object of the present invention to provide a method for producing difluoroacetyl chloride efficiently from a 1-alkoxy-1,1,2,2-tetrafluoroethane.

Means for Solving the Problems

The present inventors have made extensive researches on the method for efficiently converting difluoroacetyl fluoride, which can be obtained by thermal decomposition of a 1-alkoxy-1,1,2,2-tetrafluoroethane (ATFE), to difluoroacetyl chloride. As a result, the present inventors have found that it is possible to produce difluoroacetyl chloride (DFAC) quantitatively, without causing chlorination of a hydrogen atom in a difluoromethyl group, by contact of difluoroacetyl fluoride (DFAF) and calcium chloride under heating conditions. The present inventors have also found that the difluoroacetyl chloride can be obtained in one process step with high selectivity and high yield, without the need to extract difluoroacetyl chloride as an intermediate, by the application of a similar reaction process to ATFE. The present invention is based on these findings.

Herein, it is conceivable to propose: an indirect reaction process that uses ATFE as a starting material and goes through difluoroacetyl fluoride as an intermediate; and a direct reaction process that obtains a target compound directly from ATFE. In the indirect reaction process, a fluorine-containing organic compound such as monofluoromethane is generated as a by-product. By contrast, a chlorine-containing organic compound such as monochloromethane is generated as a by-product in the direct reaction process. Even though both of these organic compounds are useful and have a certain range of uses, the chlorine-containing organic compound is easier to decompose and is preferred in terms of waste management as compared to the fluorine-containing organic compound.

Namely, the present invention includes the following aspects.

[Inventive Aspect 1]
A production method of difluoroacetyl chloride, comprising a chlorination step of bringing a raw material containing therein at least either a 1-alkoxy-1,1,2,2-tetrafluoroethane or difluoroacetyl fluoride into contact with calcium chloride at a reaction enabling temperature at which the at least either the 1-alkoxy-1,1,2,2-tetrafluoroethane or difluoroacetyl fluoride can undergo reaction.

[Inventive Aspect 2]
The production method according to Inventive Aspect 1, wherein the raw material contains at least the 1-alkoxy-1,1,2,2-tetrafluoroethane.

[Inventive Aspect 3]
The production method according to Inventive Aspect 1 or 2, wherein the raw material contains at least the 1-alkoxy-1,1,2,2-tetrafluoroethane and the difluoroacetyl fluoride.

[Inventive Aspect 4]

The production method according to any one of Inventive Aspects 1 to 3, wherein the chlorination step is performed in a gas-phase continuous-flow system.

[Inventive Aspect 5]

The production method according to any one of Inventive Aspects 1 to 4, wherein the chlorination step is performed at a temperature of 50 to 400° C.

[Inventive Aspect 6]

The production method according to any one of Inventive Aspects 1 to 5, further comprising a separation step of removing, from a product composition obtained in the chlorination step and containing therein an alkyl halide and difluoroacetyl chloride, the alkyl halide.

[Inventive Aspect 7]

The production method according to any one of Inventive Aspects 1 to 6, wherein the 1-alkoxy-1,1,2,2-tetrafluoroethane is 1-methoxy-1,1,2,2-tetrafluoroethane.

[Inventive Aspect 8]

The production method according to any one of Inventive Aspects 1 to 7, wherein the difluoroacetyl fluoride is obtained by thermal decomposition of an 1-alkoxy-1,1,2,2-tetrafluoroethane.

[Inventive Aspect 9]

A production method of 2,2-difluoroethyl alcohol, comprising a catalytic reduction step of causing catalytic reduction of the difluoroacetyl chloride obtained by the production method according to any one of Inventive Aspects 1 to 8.

[Inventive Aspect 10]

The production method according to Inventive Aspect 9, wherein the catalytic reduction step is performed in the presence of a palladium catalyst.

The chlorination step of the present invention makes it possible that the 1-alkoxy-1,1,2,2-tetrafluoroethane and the difluoroacetyl fluoride can be efficiently and selectively converted to the difluoroacetyl chloride by the same process operation under substantially the same reaction conditions. Further, the adoption of such a chlorination step makes it possible that the 2,2-difluoroethyl alcohol can be obtained with high selectivity and high yield with the use of the 1-alkoxy-1,1,2,2-tetrafluoroethane as the raw material.

BRIEF DESCRIPTION OF THE DRAWINGS

FIG. 3 is a schematic view of a reaction device used in Examples 3 and 4.

FIG. 4 is a schematic view of a reaction device used in Thermal Decomposition Examples 1 to 3 and Examples 7 and 8.

DETAILED DESCRIPTION OF THE EMBODIMENTS

Figure 1:
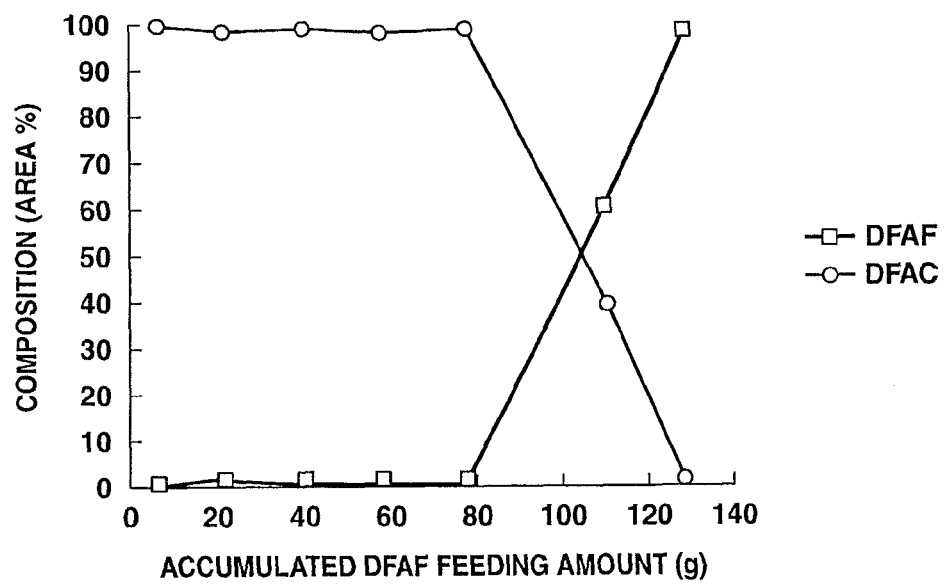
FIG. 1 is a graph showing the reaction results of Example 1.

Hereinafter, the present invention will be described below in detail.

A production method of difluoroacetyl chloride according to the present invention includes a reaction step (chlorination step) of bringing a raw material containing at least either a 1-alkoxy-1,1,2,2-tetrafluoroethane (ATFE) or difluoroacetyl fluoride (DFAF) into contact with calcium fluoride at a reaction enabling temperature at which the at least either the 1-alkoxy-1,1,2,2-tetrafluoroethaneor difluoroacetyl fluoride can undergo reaction.

In the present invention, each of reactions involved in the chlorination step is quantitative. The respective reactions of the chlorination step are represented by the following reaction schemes (1) and (2).

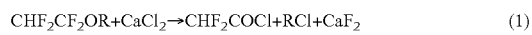

$$CHF_2CF_2OR + CaCl_2 \rightarrow CHF_2COCl + RCl + CaF_2 \quad (1)$$

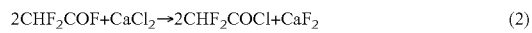

$$2CHF_2COF + CaCl_2 \rightarrow 2CHF_2COCl + CaF_2 \quad (2)$$

There is no particular limitation on R in the 1-alkoxy-1,1,2,2-tetrafluoroethane of the general formula: $CHF_2CF_2OR$ (where R is a monovalent organic group) used as the starting material of the reaction scheme (1) because R serves as a leaving group. Examples of R are $C_1$-$C_8$ straight, branched or cyclic alkyl group or fluorine-containing alkyl group and aryl group. Among others, the alkyl group or fluorine-containing alkyl group is preferred. The alkyl group is more preferred. Still more preferred is lower alkyl. Herein, the term "lower alkyl" refers to an alkyl group of 1 to 4 carbon atoms.

Examples of the $C_1$-$C_8$ straight or branched alkyl group are methyl, ethyl, n-propyl, isopropyl, n-butyl, s-butyl, t-butyl, n-pentyl and isopentyl. Of these, methyl, ethyl, n-propyl, isopropyl, n-butyl, s-butyl and t-butyl are categorized as the lower alkyl group.

Examples of the $C_1$-$C_8$ cyclic alkyl group are cyclobutyl, cyclopentyl, 2-methylcyclopentyl, 3-methylcyclopentyl, 2-ethylcyclopentyl, 3-ethylcyclopentyl, cyclohexyl, 2-methylcyclohexyl, 3-methylcyclohexyl, 4-methylcyclohexyl, 2-ethylcyclohexyl, 3-ethylcyclohexyl, 4-ethylcyclohexyl, cycloheptyl, 2-methylcycloheptyl, 3-methylcycloheptyl and 4-methylcycloheptyl.

Examples of the aryl group are phenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,6-dimethylphenyl, 2-methoxyphenyl, 3-methoxyphenyl, 4-methoxyphenyl, 1-naphthyl and 2-naphthyl.

Examples of the $C_1$-$C_8$ fluorine-containing alkyl group are fluoromethyl, difluoromethyl, trifluoromethyl, chlorofluoromethyl, chlorodifluoromethyl, bromofluoromethyl, bromodifluoromethyl, 2,2,2-trifluoroethyl, pentafluoroethyl, 2,2,3,3,3-pentafluoropropyl, n-hexafluoropropyl and hexafluoroisopropyl.

It is feasible to obtain the 1-alkoxy-1,1,2,2-tetrafluoroethane by a known production process. One example of such production process is to react an alcohol (R'OH) with tetrafluoroethylene in the presence of a base as represented by the following reaction scheme (3).

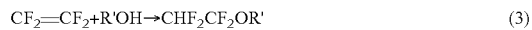

$$CF_2=CF_2 + R'OH \rightarrow CHF_2CF_2OR' \quad (3)$$

More specifically, 1-methoxy-1,1,2,2-tetrafluoroethane can be synthesized by reaction of methanol and tetrafluoroethylene in the presence of potassium hydroxide (see J. Am. Chem. Soc., 73, 1329 (1951)).

Specific examples of the 1-alkoxy-1,1,2,2-tetrafluoroethane used in the present invention include, but are not limited to, 1-methoxy-1,1,2,2-tetrafluoromethane (also referred to as "$CHF_2CF_2OMe$" or "HFE-254 pc"), 1-ethoxy-1,1,2,2-tetrafluoroethane (also referred to as "$CHF_2CF_2OEt$" or "HFE-374 pc-f"), 1-(n-propoxy)-1,1,2,2-tetrafluoroethane, 1-isopropoxy-1,1,2,2-tetrafluoroethane, 1-(n-butoxy)-1,1,2,2-tetrafluoroethane, 1-(s-butoxy)-1,1,2,2-tetrafluoroethane, 1-(t-butoxy)-1,1,2,2-tetrafluoroethane, 1-trifluoromethoxy-1,1,2,2-tetrafluoroethane, 1-difluoromethoxy-1,1,2,2-tetrafluoroethane, 1-(2,2,2-trifluoroethoxy)-1,1,2,2-tetrafluoroethane, 1-pentafluoroethoxy-1,1,2,2-tetrafluoroethane, 1-(2,2,2,3,3-pentafluoropropoxy)-1,1,2,2-tetrafluoroethane and 1-hexafluoroisopropoxy-1,1,2,2-tetrafluoroethane.

Among others, preferred are HFE-254 pc and HFE-374 pc-f each of which is low in molecular weight and easy to evaporate.

It is feasible to obtain the difluoroacetyl fluoride (DFAF) by any production process. Any of the above-mentioned processes, such as: (1) thermal decomposition of a 1-alkoxy-1,1,2,2-tetrafluoroethane represented by $CHF_2CF_2OR'$ in the presence of sulfur trioxide and fluorosulfuric acid (Non-Patent Document 1); and (2) production of difluoroacetyl fluoride by thermal decomposition of a 1-alkoxy-1,1,2,2-tetrafluoroethane in the presence of a catalyst (Patent Document 4), is applicable.

In the present invention, the difluoroacetyl fluoride is preferably obtained by thermal decomposition of a 1-alkoxy-1,1,2,2-tetrafluoroethane. This thermal decomposition reaction is represented by the following reaction scheme (4) where R' is an alkyl group.

$$CHF_2CF_2OR' \rightarrow CHF_2COF + R'F \quad (4)$$

In the thermal decomposition reaction, metal oxide, partially fluorinated metal oxide, metal fluoride, phosphoric acid or phosphate is used as a solid catalyst. Specific examples of the catalyst are a metal oxide or partially fluorinated metal oxide as disclosed in Patent Document 2 (Japanese Laid-Open Patent Publication No. H8-92162) and a metal fluoride.

The thermal decomposition temperature is set depending on the kind of the catalyst and the contact time and is generally in the range of 100 to 400° C., preferably 110 to 350° C., more preferably 130 to 320° C., still more preferably 130 to 260° C., most preferably 140 to 200° C. The reaction time (contact time) is set depending on the reaction temperature and is generally in the range of 0.1 to 1000 seconds, preferably 1 to 500 seconds, more preferably 10 to 300 seconds.

By the thermal decomposition of the 1-alkoxy-1,1,2,2-tetrafluoroethane, equivalent molar amounts of difluoroacetyl fluoride and alkyl fluoride (R'F) are generated. Further, unreacted 1-alkoxy-1,1,2,2-tetrafloroethane may be contained in the reaction product of the thermal decomposition. It is preferable to separate and remove the alkyl fluoride from the difluoroacetyl fluoride, or at least reduce the amount of the alkyl fluoride contained in the reaction product, in advance of the chlorination step.

There is no particular limitation on the process for separation of the alkyl fluoride. In view of the fact that not only the alkyl fluoride but also the difluoroacetyl fluoride and unreacted ATFE are contained in the reaction product, a distillation process using a difference between the boiling points of the alkyl fluoride and the other components or a extraction process using a difference between the solubility of the alkyl fluoride and the other components in water or solvent is herein applicable.

The distillation process can be performed by any ordinary distillation technique using a distillation column. In the case where there is a large boiling point difference between the distillation target, that is, alkyl fluoride and the other components such as difluoroacetyl fluoride (boiling point: 0° C.) and unreacted ATFE, it is feasible to easily separate the alkyl fluoride by simply cooling liquefaction. For example, when the ATFE is HFE-254 pc (boiling point: 40° C.), the alkyl fluoride is monofluoromethane (boiling point: −78° C.) so that there is a large boiling point difference between HFE-254 pc and monofluoromethane. The monofluoromethane can be thus easily separated as a low-boiling fraction from a high-boiling fraction mixture of the difluoroacetyl fluoride and HFE-254 pc by cooling liquefaction at −20 to −78° C. In the case of using the distillation column, the distillation process is performed with the use of a packed column, bubble-cap column or empty column at a column top temperature of at around −78° C. and a column bottom temperature of about 0 to 50° C.

It is conceivable to further distillate the mixture of the difluoroacetyl fluoride and ATFE so that the difluoroacetyl fluoride and ATFE can be separated as respective components and used separately in the subsequent chlorination step. However, the mixture of the difluoroacetyl fluoride and ATFE can be used, as it is without separation, in chlorination step of the present invention. There is no particular limitation on the component ratio of the mixture of the difluoroacetyl fluoride and ATFE as the difluoroacetyl fluoride and ATFE undergo the chlorination reaction under substantially the same reaction conditions. The difluoroacetyl fluoride, the ATFE or the mixture thereof, even if containing monofluoromethane, is used in the chlorination step of the present invention because the monofluoromethane is stable in the chlorination step. Moreover, a hydrocarbon by-product such as ethylene, propylene etc. may be contained in the thermal decomposition product. It is preferable to remove such a hydrocarbon by-product from the thermal decomposition product although the thermal decomposition product can be used in the chlorination step without separation of the hydrocarbon by-product.

[Chlorination Step]

In the chlorination step, the difluoroacetyl fluoride, the ATFE or the mixture of the difluoroacetyl fluoride and ATFE is chlorinated with calcium chloride so as to thereby convert the difluoroacetyl fluoride and the ATFE to the difluoroacetyl chloride.

The calcium chloride ($CaCl_2$) used in the chlorination step is preferably in the form of an anhydride. The calcium chloride does not particularly need to be high in purity. As the calcium chloride, there can be used any general-purpose product available as a reagent, a chemical raw material or a drying agent. Further, the calcium chloride can be in any shape. In the case of a flow-bed system or a batch system, the calcium chloride is preferably in powdery form. In the case of a continuous-flow system, the calcium chloride is preferably in granular form. There is no particular limitation on the particle size of the calcium chloride. It is preferable to use the calcium chloride of readily available size. For ease of handling, the calcium chloride is particularly preferably in granular form mainly containing particles with a maximum length of the order of 1 to 20 mm. In the case where crystalline water is contained in the calcium chloride, it is preferable to obtain the calcium chloride in substantially anhydrous form by pretreatment of filling the calcium chloride into a reaction vessel and heating the calcium chloride in the reaction vessel under the flow of an inert gas such as nitrogen. The temperature of the pretreatment is set depending on the water content, treatment time, particle shape, particle size etc. of the calcium chloride and is preferably in the range of 150 to 350° C.

It is preferable to perform the chlorination step in a continuous-flow system although the chlorination step can be performed in either a continuous-flow system or a batch system. Further, it is preferable to perform the chlorination step in a gas phase for convenience and facilitation although the chlorination step can be performed in either a gas phase or a liquid phase. In the continuous-flow system, the difluoroacetyl fluoride and ATFE are quantitatively converted to the difluoroacetyl chloride etc. as indicated in the reaction schemes (1) and (2) by heating the granular calcium chloride packed in the reaction tube at a temperature sufficient for conversion of the difluoroacetyl fluoride or ATFE to the difluoroacetyl chloride, that is, a reaction enabling temperature at which the difluoroacetyl fluoride or ATFE can undergo reaction, and then, feeding the difluoroacetyl fluoride, the ATFE or the mixture thereof in gaseous form through the calcium chloride in the reaction tube.

In such a gas-phase continuous-flow system, either a fixed bed or a flow bed is applicable. In the case of using the granular calcium chloride, the fixed bed is preferred for prevention of powdering and for ease of removal. In general, the reaction between a gas and a solid occurs only at a surface of the solid. It is often that the inside of the solid is not involved in the gas-solid reaction. In the chlorination step of the present invention, by contrast, the granular calcium chloride maintains its form after the reaction so that substantially the whole of the calcium chloride can contribute to the reaction. When the residue meaning after the use of the calcium chloride is analyzed by XDF (powder X-ray diffraction), the diffraction peak pattern of the residue is in agreement with that of calcium fluoride ($CaF_2$). There is no peak attributed to the calcium chloride. It is thus apparent that even the inside of the calcium chloride is involved in the reaction. The by-produced calcium fluoride can be treated by contact with concentrated sulfuric acid in a kiln and used as a raw material for production of hydrogen fluoride or optical crystal. Further, the chlorination step may be performed in the presence of an inert gas. Examples of the inert gas are nitrogen, argon and rare gas. For ease of handling and availability, nitrogen, argon or helium is preferably used. In the case of using the inert gas, there is no particular limitation on the ratio of the inert gas. However, the recovery rate of the difluoroacetyl chloride may be deteriorated if the inert gas is present in too large amount. Under normal conditions, the feeding rate of the inert gas is preferably lower than the feeding rate of the organic raw material such as ATFE, difluoroacetyl fluoride or mixture thereof.

In the chlorination step, the pressure is set arbitrarily and is generally of the order of 0.05 to 1 MPa. It is preferable to perform the chlorination step substantially at around atmospheric pressure. The reaction temperature is set depending on the kind of the raw material, the retention time etc. of the chlorination step and is preferably in the range of 50 to 400° C., more preferably 100 to 300° C., still more preferably 100 to 250° C. If the reaction temperature is lower than 50° C., the production efficiency of the difluoroacetyl chloride is unfavorably decreased due to low reaction rate. If the reaction temperature exceeds 400° C., the yield of the difluoroacetyl chloride is unfavorably decreased due to decomposition of difluoroacetyl chloride. In the case where the generation of a chlorine-containing organic compound e.g. monochloroethane as a by-product is not desired when HFE-374 pc-f is used as the raw material, the reaction temperature is preferably set to 250 to 300° C. The monochloroethane may not be sufficiently decomposed into ethylene and hydrochloric acid under temperature conditions lower than 250° C.

The retention time is set depending on the reaction temperature and is generally in the range of 1 to 1000 seconds, preferably 10 to 700 seconds, more preferably 50 to 500 seconds. If the retention time is shorter than 1 second, the reaction may not be completed. If the retention time exceeds 1000 seconds, the reaction takes place but causes increase in equipment size so that the productivity of the difluoroacetyl chloride relative to the equipment size becomes deteriorated. In the case of using the reaction tube in the continuous-flow system, heat of 10 to 30° C. (called "heat spot") is locally generated in the vicinity of the inlet of the reaction tube at an early stage after the initiation of the reaction. This heat spot gradually shifts toward the outlet of the reaction tube. The conversion rate suddenly decreases when the heat spot reaches the vicinity of the outlet of the reaction tube. By monitoring such a phenomenon, the degree of consumption of the calcium chloride can be checked so as to determine the time for replacement of the calcium chloride. In the continuous-flow reaction system, it is preferable to set the retention time long (i.e. set the feeding rate of the raw material low) because fresh calcium chloride is present in a large excessive amount at the early stage of the reaction but decreases in amount as the heat spot nears the vicinity of the outlet of the reaction tube. In order to reduce the frequency of replacement of the calcium chloride, it is preferable to use the equipment of larger size within the common sense of those skilled in the art. The reaction tube is preferably formed of or with a lining of stainless steel, Monel (trademark), Inconel (trademark), Hastelloy (trademark) or fluoro resin.

In addition to the difluoroacetyl chloride, unreacted raw material such as ATFE or difluoroacetyl fluoride, alkyl halide (chlorine-containing organic compound e.g. monochloromethane) and decomposition products thereof may be contained in the product composition of the chlorination step. It is feasible to separate these compounds by any ordinary purification process. For example, the difluoroacetyl chloride (boiling point: 28° C.) and monochloromethane ($CH_3Cl$, boiling point: −24° C.) produced by chlorination of the raw material containing HFE-254 can be separated by distillation etc. because of their large point difference. The above explanation about the distillation separation of the alkyl fluoride from the thermal decomposition product is applicable to the distillation separation of the alkyl chloride. The operation conditions are different but can be easily adjusted by those skilled in the art. Further, it is feasible to recover the alkyl halide such as monochloromethane by separating the difluoroacetyl chloride by distillation and removing an acid component from the distillation residue by treatment with water or aqueous alkaline solution. The thus-obtained difluoroacetyl chloride composition obtained in the chlorination step can be used, as it is without separation, as difluoroacetyl chloride in various reactions.

When HFE-254 pc is used as the ATFE, alkyl halide (RCl) such as monofluoromethane is generated as a by-product. In the case where such a by-product is not desired, HFE-374 pc-f ($CHF_2CF_2OCH_2CH_3$) or the like can alternatively be used as the raw material. In this case, there occur ethylene and hydrochloric acid as by-products in place of the chlorine-containing organic compound such as alkyl halide. This makes it possible to avoid the entry of the chlorine-containing organic compound into the product and reduce the load of purification operation of the difluoroacetyl chloride.

[Catalytic Reduction Step]

A production method of 2,2-difluoroethyl alcohol according to the present invention includes a catalytic reduction step of causing catalytic reduction of difluoroacetyl chloride. The catalytic reduction step can be performed in a gas phase or liquid phase.

The reaction of the catalytic reduction step is represented by the following reaction scheme (5).

$$CHF_2COCl + 2H_2 \rightarrow CHF_2CH_2OH + HCl \qquad (5)$$

In the catalytic reduction step, it is feasible to use the difluoroacetyl chloride obtained in the above chlorination step although difluoroacetyl chloride can be obtained by any of the production processes mentioned in "Background Art". It is preferable that the difluoroacetyl chloride does not substantially contain difluoroacetyl fluoride. If the difluoroacetyl fluoride is contained in the difluoroacetyl chloride, a stable salt is formed by fluorination of a noble metal of the catalyst so as to cause a deterioration in the activity of the catalyst. As a result, the yield and selectivity of the 2,2-difluoroethyl alcohol is decreased due to generation of 2,2-difluoroethyl 2,2-difluoroacetate by reaction of the unreacted difluoroacetyl fluoride with the produced 2,2-difluoroethyl alcohol.

The catalyst can be of any metal usable in any known catalytic reduction by hydrogen in the catalytic reduction step. Preferably, a noble metal is used as the catalyst. Preferred examples of the noble metal used as the catalyst are palladium (Pd), platinum (Pt), rhodium (Rh), ruthenium (Ru) and iridium (Ir). Among others, Pd is more preferred. In order to efficiently utilize the noble metal, the noble metal is preferably supported on a support such as activated carbon, alumina, barium sulfate, calcium carbonate, strontium carbonate or silica gel. It is particularly preferable to support the noble metal on the activated carbon. Specific examples of the catalyst are: palladium supported on activated carbon; palladium hydroxide supported on activated carbon; palladium supported on barium sulfate; palladium supported on calcium carbonate; palladium supported on strontium carbonate; palladium supported on silica gel; platinum supported on activated carbon; ruthenium supported on activated carbon; and rhodium supported on activated carbon. In particular, preferred is palladium supported on activated carbon (Pd/C). The amount of the metal supported is generally 0.1 to 10 mass %, preferably 0.2 to 5 mass %, based on the total amount of the catalyst including the support.

In the gas-phase reaction system, it is preferable to use hydrogen in an amount of 5 to 100 mol, more preferably 10 to 30 mol, per 1 mol of the difluoroacetyl chloride. If the amount of the hydrogen used is less than 5 mol (i.e. the reaction system is in a low-hydrogen-content state), not only deterioration of the conversion rate but also deactivation of the catalyst may unfavorably occur. If the amount of the hydrogen used exceeds 100 mol, the feeding rate of the difluoroacetyl chloride is decreased so as to cause deterioration in productivity under the conditions of the same reaction vessel and the same contact time.

The contact time is generally 1 to 200 seconds, preferably 10 to 60 seconds. If the contact time is shorter than 1 second, the conversion rate is unfavorably deteriorated. If the contact time is longer than 200 second, the productivity of the 2,2-difluoroethyl alcohol relative to the volume of the reaction vessel is unfavorably deteriorated. The reaction temperature is preferably 150 to 300° C., more preferably 170 to 230° C. If the reaction temperature is lower than 150° C., the conversion rate is deteriorated. If the reaction temperature is higher than 300° C., there is a fear of not only sintering of the catalyst but also side reaction such as hydrogenolysis. In the gas-phase reaction system, the reaction is performed substantially at around atmospheric pressure. The reaction can alternatively be performed at a pressure of about 0.05 to 1 MPa. Further, the reaction may be performed upon introduction of an inert gas such as argon or nitrogen into the reaction vessel.

In the liquid-phase reaction system, a heterogeneous catalyst is preferred for easy separation of the catalyst although the catalyst can be either a homogeneous catalyst or a heterogeneous catalyst. The above-mentioned supporting catalyst, more specifically noble metal-supporting catalyst, is thus preferably used. The amount of the catalyst used is set depending on the kind of the catalyst and is generally 0.0001 to 1 mol %, more preferably 0.001 to 0.1 mol %.

Further, a reaction solvent can be used in the liquid-phase reaction system. As the reaction solvent, alcohols, hydrocarbons, ethers, carboxylic acids, esters, amides and water are usable. Specific examples of the reaction solvent are methanol, ethanol, benzene, toluene, xylene, ethylbenzene, isopropylbenzene, tetralin, mesitylene, tetrahydrofuran, diethyl ether, acetic acid, ethyl acetate and dimethylformamide. The hydrocarbons and ethers are more preferred in view of the fact that the alcohols are difficult to separate from the 2,2-difluoroethyl alcohol. Further, the use of 2,2-difluoroethyl alcohol, which is the target compound, as the solvent is preferred so as to omit the separation operation of the solvent. The use of 2,2-difluoroethyl 2,2-difluoroethylacetate ($CHF_2COOCH_2CHF_2$), which may be generated as a by-product, is acceptable under the above reaction conditions. These solvents can be used solely or in combination of two or more kinds thereof.

The pressure of the hydrogen is set depending on the reaction conditions such as the kinds of the solvent and catalyst and is generally about 1 to 10 MPa, preferably 0.5 to 5 MPa. If the hydrogen pressure is lower than 0.5 MPa, the reaction may become slow. If the hydrogen pressure exceeds 5 MPa, the equipment needs to be pressure resistant. The reaction may be performed upon introduction of an inert gas such as argon or nitrogen into the reaction vessel.

The reaction temperature is generally in the range from −20° C. to a boiling point of the solvent and is preferably about 0 to 50° C. The object of the reaction can be sufficiently achieved even at a room temperature of 10 to 30° C.

It is unlikely that the catalyst will deteriorate in the case of using, as the raw material, the difluoroacetyl chloride containing substantially no difluoroacetyl fluoride. The activity of the catalyst may however become deteriorated with the passage of time in the gas-phase reaction system. In such a case, it is feasible to reactivate the catalyst by stopping the feeding of the difluoroacetyl fluoride and feeding hydrogen to the catalyst at 250 to 350° C. At this time, the hydrogen may be used while diluted with nitrogen or argon. In the liquid-phase reaction system, it is feasible to, when the activity of the supported catalyst becomes deteriorated during use, reactivate the catalyst by feeding hydrogen to the catalyst at 250 to 350° C. in the same manner as above. The hydrogen may also be used while diluted with nitrogen or argon at this time.

EXAMPLES

The present invention will be described in more detail below by way of the following examples. It should be noted that the following examples are not intended to limit the present invention thereto. Unless otherwise specified, the composition and purity of organic substances were analyzed by a gas chromatograph with a FID detector; and each composition analysis value is in units of "area % (hereinafter simply referred to as "%")". Further, a column according to "EPA Method 624" was used in the analysis of the organic substance composition unless otherwise specified.

Reference Example 1

Sensitivity Check of FID Detector

A gas chromatograph was equipped with a column according to "EPA Method 624". On the other hand, an equivalent molar composition was prepared from samples of monofluoromethane and difluoroacetyl fluoride. The area of each component in the prepared composition was measured by the gas chromatograph. According to the measurement results, the area ratio was monofluoromethane: $CHF_2COF=2.41:1.00$.

Raw Material Preparation Example 1

Preparation of Difluoroacetyl Fluoride

An aluminum phosphate catalyst was prepared by compression molding aluminum phosphate available from Aldrich Chemical Co. into pellets of 5 mm φ×5 mm L and firing the pellets at 700° C. for 5 hours under a nitrogen flow atmosphere. Then, a stainless steel reaction tube (inner diameter φ: 37.1 mm, length L: 500 mm) having a carburetor was packed with 200 cc of the prepared catalyst. While flowing nitrogen at 15 cc/min into the reaction tube, the reaction tube was heated externally by an electric furnace. When the temperature of the catalyst reached 50° C., hydrogen fluoride (HF) was introduced at a rate of 0.6 g/min into the reaction tube through the carburetor. The temperature of the catalyst was slowly raised to 300° C. while maintaining the flow of the HF. In this state, the catalyst was held at 300° C. for 5 hours. After that, the heater setting temperature was lowered to 200° C. When the temperature of the catalyst reached 200° C., the flow of the HF was stopped; and the flow rate of the nitrogen was increased to 200 cc/min. The catalyst was then held for 2 hours. Subsequently, 1-methoxy-1,1,2,2-tetrafluoroethane (HFE-254 pc) was fed at a rate of 0.2 g/min into the reaction tube through the carburetor. After a lapse of 30 minutes, the flow of the nitrogen was stopped so as to feed only the HFE-254 pc into the reaction tube. The resulting gas product was sampled under a steady state and analyzed by the gas chromatograph. It was confirmed by the analysis results that difluoroacetyl fluoride ($CHF_2COF$) and methyl fluoride ($CH_3F$) were contained substantially quantitatively in the gas sample. The above-obtained crude difluoroacetyl fluoride was subjected to distillation, thereby obtaining purified difluoroacetyl fluoride with a purity of 99% or higher.

Catalyst Preparation Example 1

Activation of Pd/C Catalyst

A stainless steel reaction tube having an inner diameter of 37 mm and a length of 500 mm was packed with 2% Pd/activated carbon catalyst (280 cc) available from Evonik Degussa Japan Co., Ltd. Nitrogen and hydrogen were mixed together and fed into the reaction tube at 100 cc/min and 50 cc/min, respectively, at room temperature. The reaction tube was heated so as to slowly raise the temperature of the catalyst to 350° C. over 8 hours and not to cause local heat generation in the catalyst. When the temperature of the catalyst reached 350° C., the flow rate of the hydrogen was increased by 50 cc/min every 30 minutes. The flow rate of the hydrogen was finally maintained at 518 cc/min for 8 hours. After that, the reaction tube was slowly cooled down to room temperature while only flowing the nitrogen into the reaction tube. In the above catalyst activation operation, the flow rate of the hydrogen was decreased to 10 cc/min or lower upon detection of local heat generation (heat spot). After confirming that such local heat generation settled down, the flow rate of the hydrogen gas was gradually returned to the predetermined level.

Example 1

A stainless steel reaction tube having an inner diameter of 23 mm and a length of 400 mm was packed with granular anhydrous calcium chloride (63 g, 120 cc; available from Junsei Chemical Co., Ltd. (particle size: about 2.5 to 3.5 mm)). While flowing nitrogen at 50 cc/min into the reaction tube, the reaction tube was heated at a setting temperature of 160° C. The flow of the nitrogen was stopped simultaneously with feeding the difluoroacetyl fluoride, which had been obtained in Raw Material Preparation Example 1, into the reaction tube at a rate of 0.3 g/min (retention time: 66 seconds). It was observed that a heat spot of 10 to 20° C. was generated in the vicinity of the inlet of the reaction tube and shifted toward the outlet of the reaction tube with the passage of time. The outlet gas was sampled and analyzed over time by the gas chromatograph. It was confirmed by the experimental results that difluoroacetyl chloride (DFAC) and difluoroacetyl fluoride (DFAF) were contained in the gas sample. The experimental results are graphed in FIG. 1.

Example 2

Figure 2:
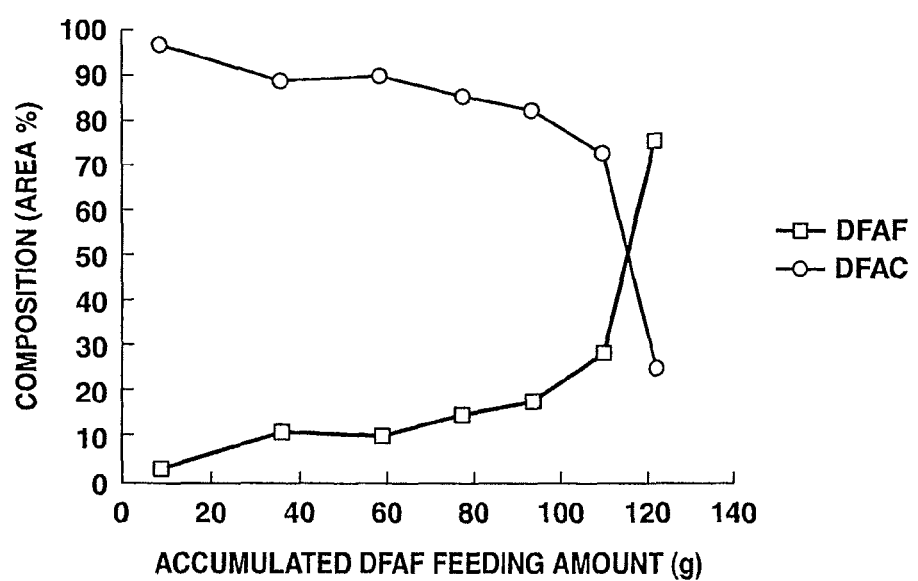
FIG. 2 is a graph showing the reaction results of Example 2.

Reaction experiment was performed in the same manner as in Example 1, except that the temperature of the reaction tube was set to 100° C. The experimental results are graphed in FIG. 2.

Example 3

As shown in FIG. 3, a stainless steel reaction tube I having an inner diameter of 45 mm and a length of 1500 mm and having three tube-heating mantles separately operable under PID (proportional-integral-derivative) control was packed with granular calcium chloride (993 g, 2000 cc); and a reaction tube II was packed with the Pd/C catalyst pretreated in Catalyst Preparation Example 1 and connected to the outlet side of the reaction tube I. While flowing nitrogen (100 cc/min) into the reaction tube I, the reaction tube I was heated by setting the temperatures of the electric furnaces to 150° C., 160° C. and 170° C., respectively, from the inlet side. Further, the reaction tube II was heated to 185° C. while flowing hydrogen (518 cc/min) into the reaction tube II from a branch line immediately upstream of the inlet of the reaction tube II. A raw material (DFAC: 80%, DFAF 19.3%, others: 0.7%), which had been prepared by adding the DFAF obtained in Raw Material Preparation Example 1 to the product (main components: DFAC, DFAF) of repetition of Examples 1 and 2, was fed at a rate of 0.13 g/min into the reaction tube I from the inlet side after a lapse of 3 hours from the stabilization of the temperatures of both of the reaction tubes I and II. After a lapse of 1 hour, the flow of the nitrogen was stopped. After a lapse of 750 hours, the gas product was sampled at the sampling ports A and B and analyzed by the gas chromatograph (FID). The experimental results are indicated in TABLE 1.

Example 4

Reaction experiment was performed in the same manner as in Example 3, except for, after replacing the calcium chloride in the reaction tube I with the same amount of the same kind of fresh calcium chloride, feeding the DFAF prepared in Raw Material Preparation Example 1 as the raw material (DFAC: 99% or more, others: 1% or less). After a lapse of 140 hours, the gas product was sampled at the sampling ports A and B and analyzed by the gas chromatograph (FID). The experimental results are indicated in TABLE 1.

Comparative Example 1

Reaction experiment was performed in the same manner as in Example 3, except for feeding the raw material (DFAC: 80%, DFAF: 19.3%, others: 0.7%) into the reaction tube II by bypassing the reaction tube I ($CaCl_2$ tube). After a lapse of 4 hours and a lapse of 8 hours, the gas product was sampled at the sampling ports A and B and analyzed by the gas chromatograph. The experimental results are indicated in TABLE 1.

TABLE 1

| | Elapsed time (Hr) | Sampling port A (mass %) | | Sampling port B (mass %) | | | |
|---|---|---|---|---|---|---|---|
| | | DFAC | DFAF | DFAC | DFAF | 2,2-difluoro ethanol | $CHF_2COOCH_2CHF_2$ |
| Example 3 | 750 | 99.2 | nd | nd | nd | 99.1 | 0.04 |
| Example 4 | 140 | 99.4 | tr | nd | nd | 99.3 | 0.03 |
| Comparative Example 1 | 4 | | | 0.9 | 0.1 | 97.8 | 0.01 |
| | 8 | | | nd | nd | 10.9 | 88.3 |

DFAC: difluoroacetyl chloride
DFAF: difluoroacetyl fluoride
$CHF_2COOCH_2CHF_2$: 2,2-difluoroethyl 2,2-difluoroacetate
nd: not detected
tr: trace amount detected Reference Example 2

After the completion of the reaction experiment of Example 3, the reaction tube I was cooled down to room temperature while flowing nitrogen at a rate of 50 cc/min into the reaction tube I. The content of the reaction tube I was then ground and analyzed by XRD. The analysis result was in agreement with the diffraction pattern of $CaF_2$. There was seen substantially no diffraction peak of $CaCl_2$.

Example 5

A stainless steel reaction tube having an inner diameter of 23 mm and a length of 400 mm and externally equipped with an electric furnace was packed with granular anhydrous calcium chloride (60 g, 0.541 mol, volume: 115 cc, particle size: about 2.5 to 3.5 mm; available from Junsei Chemical Co., Ltd.). While flowing nitrogen into the reaction tube at a rate of 50 cc/min, the reaction tube was heated at a setting temperature of 300° C. for 2 hours. After that, the setting temperature was controlled to 200° C. Simultaneously with feeding 1-methoxy-1,1,2,2-tetrafluoroethane (HFE-254 pc) into the reaction tube at a rate of 0.2 g/min, the flow of the nitrogen was stopped. The temperature in the vicinity of the inlet of the reaction tube, the temperature in the center of the reaction tube and the temperature in the vicinity of the outlet of the reaction tube were monitored by thermocouples. It was observed that a heat spot of 10 to 20° C. was generated in the vicinity of the inlet of the reaction tube and shifted toward the outlet of the reaction tube with the passage of time. The outlet gas was sampled and analyzed over time by the gas chromatograph. The analysis results are indicated in TABLE 2.

TABLE 2

| Example | Accumulated HFE-254pc feeding amount (mol) | Heater setting temp. ° C. | Inlet vicinity temp. ° C. | Center temp. ° C. | Outlet vicinity temp. ° C. |
|---|---|---|---|---|---|
| 5-1 | 0.042 | 200 | 213 | 203 | 199 |
| 5-2 | 0.095 | 200 | 212 | 205 | 201 |
| 5-3 | 0.167 | 200 | 207 | 209 | 203 |
| 5-4 | 0.294 | 200 | 199 | 218 | 204 |
| 5-5 | 0.498 | 200 | 198 | 202 | 217 |

| Example | Outlet gas composition (area %) | | | | | |
|---|---|---|---|---|---|---|
| | $CHF_2Cl$ | DFAF | $CH_3Cl$ | HFE-254pc | DFACl | Others |
| 5-1 | 0.146 | 0.137 | 70.303 | 0.038 | 28.742 | 0.635 |
| 5-2 | 0.401 | 0.109 | 70.762 | 0.005 | 27.992 | 0.731 |
| 5-3 | 0.368 | 0.095 | 70.660 | 0.007 | 28.429 | 0.442 |
| 5-4 | 0.308 | 0.204 | 70.314 | 0.005 | 28.698 | 0.472 |
| 5-5 | 0.417 | 10.657 | 71.386 | 0.248 | 16.220 | 1.072 |

$CHF_2Cl$: chlorodifluoromethane
DFAF: difluoroacetyl fluoride
$CH_3Cl$: methyl chloride
HFE-254pc: 1-methoxy-1,1,2,2-tetrafluoroethane
DFACl: difluoroacetyl chloride
n.d.: not detected
t.r.: trace amount detected Example 6

After the completion of the reaction experiment of Example 5, the calcium chloride was replaced with fresh one (63 g, 0.568 mol, volume: 120 cc). While flowing nitrogen into the reaction tube at a rate of 50 cc/min, the reaction tube was heated at a setting temperature of 300° C. for 2 hours. After that, the setting temperature was controlled to a temperature level as indicated in TABLE 3. Simultaneously with feeding 1-ethoxy-1,1,22-tetrafluoroethane (HFE-374 pc-f) into the reaction tube at a rate of 0.2 g/min, the flow of the nitrogen was stopped. The temperature in the vicinity of the inlet of the reaction tube, the temperature in the center of the reaction tube and the temperature in the vicinity of the outlet of the reaction tube were monitored by thermocouples. It was observed that a heat spot of several 10° C. was generated in the vicinity of the inlet of the reaction tube and shifted toward the outlet of the reaction tube with the passage of time. The outlet gas was sampled and analyzed over time by the gas chromatograph. The analysis results are indicated in TABLE 3.

TABLE 3

| Example | Accumulated HFE374pc-f feeding amount (mol) | Heater setting temp. ° C. | Inlet vicinity temp. ° C. | Center temp. ° C. | Outlet vicinity temp. ° C. |
|---|---|---|---|---|---|
| 6-1 | 0.055 | 220 | 240 | 243 | 229 |
| 6-2 | 0.181 | 250 | 251 | 283 | 265 |

TABLE 3-continued

| | | | | | |
|---|---|---|---|---|---|
| 6-3 | 0.322 | 330 | 331 | 357 | 329 |
| 6-4 | 0.366 | 330 | 337 | 350 | 330 |
| 6-5 | 0.405 | 330 | 339 | 348 | 332 |
| 6-6 | 0.553 | 330 | 334 | 345 | 338 |
| 6-7 | 0.576 | 330 | 336 | 345 | 336 |

| | Outlet gas composition (area %) | | | | | | |
|---|---|---|---|---|---|---|---|
| Example | $C_2H_4$ | $CHF_2Cl$ | DFAF | $C_2H_5Cl$ | DFACl | HFE-374pc-f | Others |
| 6-1 | 46.718 | 0.160 | n.d. | 38.496 | 12.616 | n.d. | 2.010 |
| 6-2 | 52.645 | 0.484 | n.d. | 31.484 | 13.807 | n.d. | 1.580 |
| 6-3 | 80.507 | 2.763 | n.d. | 4.675 | 11.633 | n.d. | 0.422 |
| 6-4 | 80.706 | 2.696 | n.d. | 4.377 | 11.698 | n.d. | 0.523 |
| 6-5 | 80.991 | 2.695 | n.d. | 4.395 | 11.287 | n.d. | 0.632 |
| 6-6 | 80.749 | 2.355 | n.d. | 4.035 | 12.574 | n.d. | 0.287 |
| 6-7 | 79.536 | 0.823 | t.r. | 4.767 | 14.649 | n.d. | 0.225 |

$C_2H_4$: ethylene
$CHF_2Cl$: chlorodifluoromethane
DFAF: difluoroacetyl fluoride
$C_2H_5Cl$: chloroethane
DFACl: difluoroacetyl chloride
HFE-374pc-f: 1-ethoxy-1,1,2,2-tetrafluoroethane
n.d.: not detected
t.r.: trace amount detected Catalyst Preparation Example 2

A reaction tube of stainless steel (SUS315) having a length of 1.5 mm and an inner diameter of 55 mm and surrounded by a heating mantle was packed with 2 kg of γ-alumina beads (KHS-46 available from Sumitomo Chemical Co., Ltd.). The temperature of the heating mantle was set to 50° C. While flowing nitrogen (1000 cc/min) into the reaction tube, hydrogen fluoride (HF) was vaporized by a carburetor and fed into the reaction tube at 4 g/min. It was observed that, due to the heat of absorption of HF onto γ-alumina and the heat of reaction of γ-alumina and HF, a heat spot was generated particularly in the vicinity of the reaction tube and gradually shifted toward the outlet of the reaction tube. When the highest temperature of the heat spot exceeded 300° C., the flow rate of the HF was decreased to 1 g/min or lower so as to limit such local heat generation. After confirming that the temperature reached the setting level, the flow rate of the HF was gradually returned to 4 g/min. The fluorination treatment of the γ-alumina beads was performed repeatedly by increasing the mantle setting temperature by 50° C. up to 250° C. after the heat spot reached the vicinity of the outlet of the reaction tube. Subsequently, the mantle setting temperature was controlled to 300° C.; and the flow rate of the HF was gradually increased to 20 g/min. At this time, the flow rate of the HF was decreased to 1 g/min when the temperature of the heat spot exceeded 350° C. When the heat spot was substantially no longer observed under the conditions of the mantle setting temperature of 300° C. and the HF flow rate of 20 g/min, the fluorination treatment was continued under the same conditions for further 24 hours. The reaction tube was cooled down by stopping the energization of the heating mantle while only flowing nitrogen into the reaction tube. With this, fluorinated alumina catalyst was obtained.

Thermal Decomposition Example 1

Thermal decomposition experiment was conducted using a thermal composition device shown in FIG. 4.

In the device of FIG. 4, a reaction tube 71 of stainless steel having an inner diameter of 37 mm and a length of 500 mm was provided. A sampling port 73 was located at the outlet side of the reaction tube 71. An electric furnace 72 was externally located around the reaction tube 71. On the outlet side of the reaction tube 71, an empty trap 74 of polyethylene, a coiled pipe 75, a separation column 78 (−15° C.), an ice water trap 81, an aqueous basic solution trap 82 (50% aqueous KOH solution cooled with ice) and a drying tube 84 were provided and connected together by fluoro resin or polyethylene pipes. The coiled pipe 75 was held in a coolant bath of −15° C. The separation column 78 had a reflux condenser 79 held at −78° C. by a dry ice-acetone bath on a top thereof and a jacketed high-boiling-compound collector 76 held on a bottom thereof A sampling port 84 was located at the outlet side of the device. The drying tube 83 was packed with a drying agent containing synthetic zeolite 4A. The outlet of the drying tube 83 was open to an abatement system.

Before the initiation of reaction experiment, the pipe arrangement of the device of FIG. 4 was changed so as to disconnect the reaction tube 71 from the empty trap 74 and discharge the gas directly from the outlet of the reaction tube 71 to the abatement system. First, the reaction tube 71 was packed with 230 cc of the catalyst obtained in Catalyst Preparation Example 1. While flowing nitrogen into the reaction tube 71, the temperature of the electric furnace 72 was raised. When the temperature of the catalyst reached 50° C., hydrogen fluoride (HF) was introduced at 1.0 g/min into the reaction tube 71 via a carburetor. While maintaining the flow of the HF, the temperature of the catalyst was gradually raised to 350° C. Upon detection of local heat generation during the temperature rise, the flow rate of the HF was decreased to 0.1 g/min. The flow rate of the hydrogen gas was gradually returned to 0.1 g/min after confirming that such local heat generation settled down. When the temperature of the catalyst reached 350° C., the catalyst was maintained at that temperature for 30 hours. After that, the flow of the HF was stopped; and the flow rate of the nitrogen was increased to 200 cc/min. In this state, the catalyst was held for 2 hours. The temperature of the electric furnace 72 was subsequently lowered to 180° C. Then, 1-methoxy-1,1,2,2-tetrafluoroethane (HFE-254 pc) was fed at a rate of 0.2 g/min into the reaction tube 71 via a carburetor. The flow of the nitrogen was stopped immediately afterwards. The setting temperature of the electric furnace 72 was controlled in such a manner that the reaction temperature became 150° C. When the reaction system reached a steady state, the device was returned to that of FIG. 4 by connecting the outlet of the reaction tube 71 to the empty trap 74. The resulting discharge gas was passed through the empty trap 74 and the coiled pipe 75, and then, fed into the separation column 78 (−15° C.) so as to condense a high-boiling component of the discharge gas by the reflux condenser 79. The condensed high-boiling component was collected by the jacketed high-boiling-compound collector 76 (−15° C.). An uncondensed low-boiling component of the discharge gas was passed through the ice cooling trap 81, the aqueous basic solution trap 82 and the drying tube 83.

The sample taken at the sampling port 73 was analyzed by a gas chromatograph (column according to "EPA Method 624") with a FID detector. It was confirmed that the sample at the sampling port 73 had 54.291% of $CH_3F$, 22.126% of $CHF_2COF$, 23.101% of $CHF_2CF_2OMe$ (Me: methyl, the same applies to the following) and 0.482% of other compounds. Further, the sample taken at the sampling port 84 was analyzed by a gas chromatograph (Silicon Plot column) with a FID detector. It was confirmed that the sample at the sampling port 84 had less than 0.001% of $CH_4$, 0.017% of $C_2H_4$, 0.009% of $CHF_3$, 99.961% of $CH_3F$, 0.008% of $C_3H_6$ and 0.004% of other compounds. The experimental results are summarized in TABLE 4.

Thermal Decomposition Example 2

Thermal decomposition experiment was conducted in the same manner as in Thermal Decomposition Example 1, except that the reaction temperature was set to 175° C. The sample taken at the sampling port 73 was analyzed by a gas chromatograph (column according to "EPA Method 624") with a FID detector. It was confirmed that the sample at the sampling port 73 had 69.644% of $CH_3F$, 28.420% of $CHF_2COF$, 1.351% of $CHF_2CF_2OMe$ and 0.685% of other compounds. Further, the sample taken at the sampling port 84 was analyzed by a gas chromatograph (Silicon Plot column) with a FID detector. It was confirmed that the sample at the sampling port 84 had 0.024% of $CH_4$, 0.121% of $C_2H_4$, 0.126% of $CHF_3$, 99.455% of $CH_3F$, 0.003% of $C_3H_6$ and 0.271% of other compounds. The experimental results are summarized in TABLE 4.

TABLE 4

| | | Example | | |
|---|---|---|---|---|
| | | Thermal Decomposition Example 1 | Thermal Decomposition Example 2 | Thermal Decomposition Example 3 |
| Catalyst | | alumina | alumina | ($CaF_2$) |
| Raw material and feeding rate g/min | | 254pc, 0.2 g/min | 254pc, 0.2 g/min | 254pc, 0.3 g/min |
| Reaction temp. (° C.) | | 150 | 175 | 330 |
| Thermal decomposition outlet area % | $CHF_3$ | — | — | — |
| | $CH_3F$ | 54.291 | 69.544 | 68.486 |
| | DFAF | 22.126 | 28.240 | 20.460 |
| | 254pc | 23.101 | 1.351 | 7.656 |
| | $C_2H_4$ | — | — | 2.406 |
| | Others | 0.482 | 0.685 | 0.992 |
| After purification of $CH_3F$ area % | $CH_4$ | <0.001 | 0.024 | |
| | $C_2H_4$ | 0.017 | 0.121 | |
| | $CHF_3$ | 0.009 | 0.126 | |
| | $CH_3F$ | 99.961 | 99.455 | |
| | $C_3H_6$ | 0.008 | 0.003 | |
| | 254pf | — | — | |
| | Others | 0.004 | 0.271 | |

$CHF_3$: trifluoromethane
$CH_3F$: monofluoromethane
DFAF ($CHF_2COF$): difluoroacetyl fluoride
254pc: 1-methoxy-1,1,2,2-tetrafluoroethane
$C_2H_4$: ethylene
$CH_4$: methane
$C_3H_6$: propylene
"—": not detected

Example 7

Chlorination Step

A stainless steel reaction tube having an inner diameter of 23 mm and a length of 400 mm was packed with granular anhydrous calcium chloride (63 g, volume: 120 cc, particle size: about 2.5 to 3.5 mm; available from Junsei Chemical Co., Ltd.). While flowing nitrogen into the reaction tube at 50 cc/min, the reaction tube was heated to 160° C. The flow of the nitrogen was stopped simultaneously with feeding the organic substance ($CHF_2COF$: 94.181%, $CHF_2CF_2OMe$: 4.569%), which had been recovered by the jacketed high-boiling-compound collector 76 in Thermal Decomposition Example 2, into the reaction tube at a rate of 0.3 g/min. It was observed that a heat spot of 10 to 20° C. was generated in the vicinity of the inlet of the reaction tube and shifted toward the outlet of the reaction tube with the passage of time. At the time when total 77.9 g of the organic substance was fed into the reaction tube, the outlet gas was sampled and analyzed by a gas chromatograph (column according to "EPA Method 624") with a FID detector. It was confirmed that the gas sample had 1.105% of $CHF_2COF$, 4.708% of $CH_3Cl$, 0.001% of $CHF_2CF_2OMe$, 93.769% of $CHF_2COCl$ and 0.417% of other compounds. The experimental results are summarized in TABLE 5.

TABLE 5

| | | Example | |
|---|---|---|---|
| | | Example 7 | Example 8 |
| Chlorination agent | | $CaCl_2$ | $CaCl_2$ |
| Raw material and feeding rate g/min | | mixture (DFAF: 94.181%, 254pc: 4.569%), 0.3 g/min | mixture (254pc: 98.1%, DFAF: 1.1%), 0.3 g/min |
| Reaction temp. (° C.) | | 160 | 200 |
| Chlorination product area % | $CHF_2COF$ | 1.105 | 0.857 |
| | $CH_3Cl$ | 4.708 | 68.877 |
| | 254pc | 0.001 | 0.341 |
| | $CHF_2COCl$ | 93.769 | 28.863 |
| | Others | 0.417 | 1.062 |

DFAF ($CHF_2COF$): difluoroacetyl fluoride
254pc: 1-methoxy-1,1,2,2-tetrafluoroethane
$CH_3Cl$: monochloromethane
$CHF_2COCl$: difluoroacetyl chloride

Thermal Decomposition Example 3

After the analysis of Example 7, the raw material was changed to $CHF_2CF_2OMe$ (99.9%); and the reaction temperature was changed to 330° C. The outlet gas was sampled under a steady state (after a lapse of 30 hours) and analyzed by a gas chromatograph (column according to "EPA Method 624") with a FID detector. It was confirmed that the gas sample had 2.406% of $C_2H_4$, 68.486% of $CH_3F$, 20.460% of $CHF_2COF$, 7.656% of $CHF_2CF_2OMe$ and 0.992% of other compounds. The experimental results are summarized in TABLE 4. After that, the feeding of the raw material was stopped. The reaction tube was cooled down to room temperature by stopping the energization of the electric furnace while flowing nitrogen (100 cc/min) into the reaction tube. The content of the reaction tube was slightly colored. The content of the reaction tube had the same shape as that before the reaction with almost no powdering or aggregation. This content was ground by an agate mortar and analyzed by XRD. The analysis result was in agreement with the diffraction pattern of $CaF_2$.

Example 8

Chlorination Step

A SUS reaction tube having an inner diameter of 23 mm and a length of 400 mm was packed with granular anhydrous calcium chloride (0.57 mol, 63 g, volume: 120 cc). While flowing nitrogen into the reaction tube at 50 cc/min, the reaction tube was heated to 200° C. The flow of the nitrogen was stopped simultaneously with feeding the sample substance ($CHF_2CF_2OMe$, purity: 98.1% (main impurity: $CHF_2COF$, 1.1%)), which had been obtained by distilling the organic substance recovered by the jacketed high-boiling-compound collector 76 in Thermal Decomposition Example 1, into the reaction tube at a rate of 0.3 g/min. The gas product was collected by a dry ice trap. It was observed that a heat spot of 10 to 20° C. was generated in the vicinity of the inlet of the reaction tube and shifted toward the outlet of the reaction tube with the passage of time. At the time when total 68.5 g (0.52 mol) of the $CHF_2CF_2OMe$ was fed into the reaction tube, total 83.8 g of the gas sample was recovered from the dry ice trap (recovery rate: 97.8%). The recovered gas sample was analyzed by a gas chromatograph (column according to "EPA Method 624") with a FID detector. It was confirmed that the gas sample had 0.867% of $CHF_2COF$, 68.877% of $CH_3Cl$, 0.341% of $CHF_2CF_2OMe$, 28.863% of $CHF_2COCl$ and 1.062% of other compounds. The experimental results are summarized in TABLE 5.

Example 9

Chlorination Step

A stainless steel reaction tube having an inner diameter of 37 mm and a length of 500 mm and externally surrounded by an electric furnace was packed with granular anhydrous calcium chloride (150 g, 1.35 mol, volume: 300 cc, particle size: about 2.5 to 3.5 mm; available from Junsei Chemical Co., Ltd.). While flowing nitrogen into the reaction tube at a rate of 50 cc/min, the reaction tube was heated at a setting temperature of 300° C. for 2 hours. After that, the setting temperature was controlled to 200° C. Simultaneously with feeding 1-methoxy-1,1,2,2-tetrafluoroethane (HFE-254 pc) into the reaction tube at a rate of 0.2 g/min, the flow of the nitrogen was stopped. The temperature in the vicinity of the inlet of the reaction tube, the temperature in the center of the reaction tube and the temperature in the vicinity of the outlet of the reaction tube were monitored by thermocouples. It was observed that a heat spot of 10 to 20° C. was generated in the vicinity of the inlet of the reaction tube and shifted toward the outlet of the reaction tube with the passage of time. At the time when total 132 g (1 mol) of the HFE-254 pc was fed into the reaction tube, the outlet gas was sampled and analyzed. It was confirmed that the gas sample had 70.3% of methyl chloride ($CH_3Cl$) and 28.7% of difluoroacetyl chloride ($CHF_2COCl$, DFAC). After confirming these analysis results, the feeding of the HFE-254 pc was stopped. The whole of the product collected by cooling with dry ice was transferred into a cylinder. By repeating 5 cycles of the above experimental reaction operation, total 642 g of the product was obtained. The thus-obtained product was distillated, thereby yielding DFAC (501 g) with a purity of 99.3%.

Reference Example 3

After performing one cycle of the reaction operation of Example 9, the content of the reaction tube was cooled down to room temperature while flowing nitrogen into the reaction tube at 50 cc/min. It was confirmed by observation that the shape of the tube content was maintained with almost no powdering. Further, the tube content (which was originally calcium chloride) was sampled from the inlet of the reaction tube and from the center of the reaction tube and analyzed by XRD. The analysis result was in agreement with the diffraction pattern of $CaF_2$. There was seen substantially no diffraction peak of $CaCl_2$.

Example 10

Catalytic Reduction Step

The reaction tube, in which the catalyst prepared in Catalyst Preparation Example 1 had remained packed, was heated to 185° C. while flowing hydrogen (783 cc/min) into the reaction tube. After the temperature was stabilized, the DFAC obtained in Example 9 was fed into the reaction tube at 0.05 g/min for 1 hour. The feeding rate of the DFAC was slowly increased to 0.2 g/min over 2 hours. The resulting product gas was sampled at the outlet of the reaction tube and analyzed by a gas chromatograph at the time when 96 g of the DFAC was fed into the reaction tube. It was confirmed that the gas sample had 99.17% of 2,2-difluoroethyl alcohol ($CHF_2CH_2OH$), 0.03% of $CHF_2COOCH_2CHF_2$ and a trace amount of DFAC. The above experimental operation was further continued. At the time when total 480 g of the DFAC was fed into the reaction tube, the product gas was sampled at the outlet of the reaction tube and analyzed by the gas chromatograph. It was confirmed that the gas sample had 99.14% of $CHF_2CH_2OH$, 0.02% of $CHF_2COOCH_2CHF_2$ and a trace amount of DFAC. The tendency of deterioration of the catalyst was not seen.

It has been shown by the above Examples 1 to 10 that it is possible to efficiently produce difluoroacetyl chloride by chlorination of 1-alkoxy-1,1,2,2-tetrafluoroethane or difluoroacetyl fluoride with calcium chloride and further possible to efficiently produce 2,2-difluoroethyl alcohol by catalytic reduction of the obtained difluoroacetyl chloride.

INDUSTRIAL APPLICABILITY

The production method of the present invention is useful for the production of difluoroacetyl chloride, which is suitably usable as a reagent for the introduction of a difluoromethyl group, and for the production of 2,2-difluoroethyl alcohol.

Although the present invention has been described with reference to the above embodiments, various modifications and variations of the above embodiments can be made based on the knowledge of those skilled in the art without departing from the scope of the present invention.

DESCRIPTION OF REFERENCE NUMERALS

71: Reaction tube
72: Electric furnace
73: Sampling port
74: Empty trap
75: Coiled tube
76: Jacketed high-boiling-compound collector
77: Sampling port
78: Separation column
79: Reflux condenser
80: Sampling port
81: Ice water trap
82: Aqueous basic solution trap
83: Drying tube
84: Sampling port

The invention claimed is:

1. A production method of difluoroacetyl chloride, comprising a chlorination step of bringing a raw material containing therein at least either a 1-alkoxy-1,1,2,2-tetrafluoroethane or difluoroacetyl fluoride into contact with calcium chloride at a reaction enabling temperature.

2. The production method of the difluoroacetyl chloride according to claim 1, wherein the raw material contains at least the 1-alkoxy-1,1,2,2-tetrafluoroethane.

3. The production method of the difluoroacetyl chloride according to claim 1, wherein the raw material contains at least the 1-alkoxy-1,1,2,2-tetrafluoroethane and the difluoroacetyl fluoride.

4. The production method of the difluoroacetyl chloride according to claim 1, wherein the chlorination step is performed in a gas-phase continuous-flow system.

5. The production method of the difluoroacetyl chloride according to claim 1, wherein the chlorination step is performed at a temperature of 50 to 400° C.

6. The production method of the difluoroacetyl chloride according to claim 1, further comprising a separation step of removing, from a product composition obtained in the chlorination step and containing therein an alkyl halide and difluoroacetyl chloride, the alkyl halide.

7. The production method of the difluoroacetyl chloride according to claim 1, wherein the 1-alkoxy-1,1,2,2-tetrafluoroethane is 1-methoxy-1,1,2,2-tetrafluoroethane.

8. The production method of the difluoroacetyl chloride according to claim 1, wherein the difluoroacetyl fluoride is obtained by thermal decomposition of an 1-alkoxy-1,1,2,2-tetrafluoroethane.

9. A production method of 2,2-difluoroethyl alcohol, comprising a catalytic reduction step of causing catalytic reduction of the difluoroacetyl chloride obtained by the production method according to claim 1.

10. The production method of the 2,2-difluoroethyl alcohol according to claim 9, wherein the catalytic reduction step is performed in the presence of a palladium catalyst.

* * * * *